US012428452B2

(12) United States Patent
Takata et al.

(10) Patent No.: US 12,428,452 B2
(45) Date of Patent: Sep. 30, 2025

(54) ANTI-GRAM-NEGATIVE BACTERIAL COMPOUND

(71) Applicant: Murata Manufacturing Co., Ltd., Nagaokakyo (JP)

(72) Inventors: Masachika Takata, Nagaokakyo (JP); Hirofumi Sunahara, Nagaokakyo (JP); Yuji Aso, Kyoto (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 705 days.

(21) Appl. No.: 17/242,715

(22) Filed: Apr. 28, 2021

(65) Prior Publication Data

US 2021/0261630 A1 Aug. 26, 2021

Related U.S. Application Data

(63) Continuation of application No. PCT/JP2018/040547, filed on Oct. 31, 2018.

(51) Int. Cl.

| | |
|---|---|
| ***C07K 14/32*** | (2006.01) |
| ***A23L 33/18*** | (2016.01) |
| ***A61P 31/04*** | (2006.01) |
| *A61K 38/00* | (2006.01) |

(52) U.S. Cl.

CPC .............. *C07K 14/32* (2013.01); *A23L 33/18* (2016.08); *A61P 31/04* (2018.01); *A61K 38/00* (2013.01)

(58) Field of Classification Search

CPC . C07K 14/32; A23L 33/18; A23L 2/44; A23L 3/3526; A23L 3/3571; A61P 31/04; A61K 38/00; A61K 38/17; A01N 37/46; A01N 63/22; C12N 1/205; C12R 2001/125

See application file for complete search history.

(56) References Cited

U.S. PATENT DOCUMENTS

| | | | |
|---|---|---|---|
| 5,516,682 | A | 5/1996 | Hansen |
| 2005/0271643 | A1 | 12/2005 | Sorokulova et al. |
| 2015/0125503 | A1 | 5/2015 | Hillman et al. |

FOREIGN PATENT DOCUMENTS

| | | | |
|---|---|---|---|
| JP | H08506010 | A | 7/1996 |
| JP | 2001136959 | A | 5/2001 |
| JP | 2007518394 | A | 7/2007 |
| JP | 4111489 | B2 | 7/2008 |
| JP | 2013147469 | A | 8/2013 |
| JP | 2015509945 | A | 4/2015 |
| JP | 5738561 | B2 | 6/2015 |

OTHER PUBLICATIONS

Uniprot Protein Database, P10946, accessed on Sep. 22, 2023, pp. 1-5.*

GenBank: MF399478.1, Bacillus licheniformis strain MCC 2512 lan operon, partial sequence, published 2017, pp. 1-6.*

Papanna Shobharani, Diversity in the antibacterial potential of probiotic cultures Bacillus licheniformis MCC2514 and Bacillus licheniformis MCC2512, Research in Microbiology 166 (2015) .*

Lantibiotic (A0A290WPH5_BACLI) [online], May 23, 2018, searched on Apr. 27, 2022, retrieved on May 20, 2022, UniProt, <https://rest.uniprot.org/unisave/A0A290WPH5?format=txt&versions=4>.

Lantibiotic (A0A2X1V906_PAEPO) [online], Oct. 10, 2018, Searched on Apr. 27, 2022, retrieved on May 20, 2022, UniProt <https://rest.uniprot.org/unisave/A0A2X1V906?format=txt&versions=2>.

Nickchi et al., "PEIMAN 1.0: Post-translational modification Enrichment, Integration and Matching ANalysis," Oxford University Press., Original Article, Database, vol. 2015, Article ID bav037, pp. 1-10.

Macek et al., "Protein post-translational modifications in bacteria," PubMed, Nature Portfolio, Nat Rev Microbiol. Nov. 2019., 17(11): 651-664.

Dias Bastos et al., "A glimpse into the modulation of post-translational modifications of human-colonizing bacteria," ScienceDirect, Journal of Proteomics, vol. 152, Jan. 30, 2017, pp. 254-275.

International Search Report issued for PCT/JP2018/040547, date of mailing Jan. 15, 2019.

Written Opinion of the International Searching Authority issued for PCT/JP2018/040547, date of mailing Jan. 15, 2019.

Lantibiotic (AOA285JLI1_9BACI) [online], May 23, 2018, retrieved on Dec. 28, 2018 UniProt https://www.uniprot.org/uniprot/AOA285JLI1.

Salle A. J. et al.; "Subtilin-An Antibiotic Produced by Bacillus subtilis. I. Action on Various Organisms"; Experimental Biology and Medicine, 1945, vol. 60, No. 1, pp. 60-64, table I, II, IV, etc.

Banerjee, S. et al.;"Structure and Expression of a Gene Encoding the Precursor of Subtilin, a Small Protein Antibiotic"; The Journal of Biological Chemistry, 1988, vol. 263, No. 19, pp. 9508-9514.

(Continued)

*Primary Examiner* — Lianko G Garyu
*Assistant Examiner* — Erinne R Dabkowski
(74) *Attorney, Agent, or Firm* — ArentFox Schiff LLP

(57) ABSTRACT

A consumable product having an anti-gram-negative bacterial compound with the amino acid sequence represented by the chemical formula below. Also described is a consumable product having *Bacillus subtilis* capable of producing a compound having the sequence represented by the chemical formula below. The *Bacillus subtilis* may be *Bacillus subtilis* MT2 strain (accession number: NITE BP-02767). Also described are methods of treating enteritis by administering a product as described herein to a patent in need thereof.

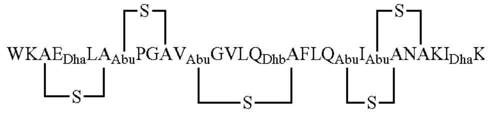

17 Claims, 8 Drawing Sheets

Specification includes a Sequence Listing.

(56) References Cited

OTHER PUBLICATIONS

Barbosa, J. et al.; "Class I and Class II Lanthipeptides Produced by Bacillus spp."; Journal of Natural Products, 2015, 78, pp. 2850-2866.
Prudencio, C.V. et al.; "Strategies for the use of bacteriocins in Gram-negative bacteria: relevance in food microbiology"; J Food Sci Technol, Sep. 2015, 52(9), pp. 5408-5417.
Zento, T. et al.; "Search and use of lactobacillus bacteriocin"; Japanese Journal of Lactic Acid Bacteria, vol. 25, No. 1, 2014, pp. 24-33, (English translation of abstract).

* cited by examiner atgtcaaagtttgatgatttcgatttggatgtagtaaaagtctctaaacaagactctaaaatcactcctcaatggaaaagtgaatcactttgtacacctgggtgtgtaactggtgtattgcaaacttgcttccttcaaacaataacttgtaactgcaaaatctctaaataa Leader peptide is encoded

MSKFDDFDLDVVKVSKQDSKITPQWKSESLCTPGCVTGVLQTCFLQTITCNCKISK

Leader peptide

SEQUENCE LISTING

```
<160> NUMBER OF SEQ ID NOS: 4

<210> SEQ ID NO 1
<211> LENGTH: 171
<212> TYPE: DNA
<213> ORGANISM: Bacillus subtilis
```

-continued

```
<400> SEQUENCE: 1

atgtcaaagt tcgatgattt cgatttggat gtagtaaaag tctctaaaca agactctaaa     60

atcactcctc aatggaaaag tgaatcactt tgtacacctg ggtgtgtaac tggtgtattg    120

caaacttgct tccttcaaac aataacttgt aactgcaaaa tctctaaata a             171


<210> SEQ ID NO 2
<211> LENGTH: 99
<212> TYPE: DNA
<213> ORGANISM: Bacillus subtilis

<400> SEQUENCE: 2

tggaaaagtg aatcactttg tacacctggg tgtgtaactg gtgtattgca aacttgcttc     60

cttcaaacaa taacttgtaa ctgcaaaatc tctaaataa                            99


<210> SEQ ID NO 3
<211> LENGTH: 56
<212> TYPE: PRT
<213> ORGANISM: Bacillus subtilis

<400> SEQUENCE: 3

Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30

Pro Gly Cys Val Thr Gly Val Leu Gln Thr Cys Phe Leu Gln Thr Ile
        35                  40                  45

Thr Cys Asn Cys Lys Ile Ser Lys
    50                  55


<210> SEQ ID NO 4
<211> LENGTH: 32
<212> TYPE: PRT
<213> ORGANISM: Bacillus subtilis

<400> SEQUENCE: 4

Trp Lys Ser Glu Ser Leu Cys Thr Pro Gly Cys Val Thr Gly Val Leu
1               5                   10                  15

Gln Thr Cys Phe Leu Gln Thr Ile Thr Cys Asn Cys Lys Ile Ser Lys
            20                  25                  30
```

ANTI-GRAM-NEGATIVE BACTERIAL COMPOUND

CROSS REFERENCE TO RELATED APPLICATIONS

The present application is a continuation of International Application No. PCT/JP2018/040547, filed Oct. 31, 2018, the entire contents of which are incorporated herein by reference.

FIELD OF THE INVENTION

The present invention relates to an anti-gram-negative bacterial compound.

BACKGROUND OF THE INVENTION

Peptides and proteins having an antimicrobial activity and produced by bacteria are known as bacteriocins. Since bacteriocins are substances derived from natural products, it is considered that human bodies are less affected by bacteriocins, compared to antimicrobial agents produced from synthetic substances. Nisin, which is a bacteriocin produced by a lactic acid bacterium, i.e., *Lactococcus lactis*, has been approved as a preservative serving as an additive to foods in many countries of the world. An example of such use is described, for example, Japanese Patent No. 4111489 and Japanese Patent No. 5738561.

It is known that bacteriocins have antimicrobial activities against related bacteria of bacteriocin-producing bacteria. Thus, it is generally considered that bacteriocins derived from bacteriocin-producing gram-positive bacteria have an antimicrobial activity against related bacteria of bacteriocin-producing bacteria that is gram-positive bacteria and no antimicrobial activity against gram-negative bacteria. Nisin has an antimicrobial activity against gram-positive bacteria but not gram-negative bacteria. Therefore, nisin has no antimicrobial activity against *Vibrio parahaemolyticus*, which is a microorganism present in fish and seafood and causing food poisoning. Bacteriocins other than nisin, for example, subtilin and entianin, have antimicrobial activities against gram-positive bacteria but not gram-negative bacteria. It is considered that this is because the adventitia of gram-negative bacteria serves as a barrier against bacteriocins derived from gram-positive bacteria. These findings are described, for example, in J. Barbosa, et al., "Class I and Class II Lanthipeptides Produced by *Bacillus* spp.", J. Nat. Prod. 2015, 78, 2850?2866; C. V. Prudencio, et al., "Strategies for the use of bacteriocins in Gram-negative bacteria: relevance in food microbiology", J Food Sci Technol (September 2015), 52 (9): 5408-5417; and Takeshi Zento et al., "search and use of *lactobacillus* bacteriocin", Japanese Journal of Lactic Acid Bacteria, Vol. 25, No. 1, 2014, Japan Society for Lactic Acid Bacteria. It is also considered that bacteriocins derived from gram-positive bacteria have no antimicrobial activity against fungi.

Because conventional bacteriocins have antimicrobial activities only against related bacteria of bacteriocin-producing bacteria, they have narrow antimicrobial spectra. There is thus a need in the art for antimicrobial compounds having a broad antimicrobial spectrum.

SUMMARY OF INVENTION

According to some aspects, the present disclosure is directed to an anti-gram-negative bacterial compound, particularly an anti-gram-negative bacterial compound having the amino acid sequence represented by chemical formula 1:

(1)

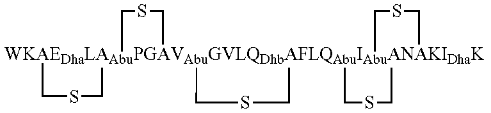

One example anti-gram-negative bacterial agent according to an aspect of the present disclosure contains an anti-gram-negative bacterial compound having the amino acid sequence represented by the chemical formula 1.

According to some aspects, a beverage or food of the present disclosure may contain an anti-gram-negative bacterial compound having the amino acid sequence represented by the chemical formula 1.

According to some aspects, the compound having the amino acid sequence represented by the chemical formula 1 as described herein may be produced by *Bacillus subtilis.*

According to some aspects, the present disclosure is also directed to *Bacillus subtilis* capable of producing a compound having the amino acid sequence represented by the chemical formula 1.

According to some aspects, the present disclosure is also directed to a beverage or food comprising *Bacillus subtilis* capable of producing a compound having the amino acid sequence represented by the chemical formula 1.

*Bacillus subtilis* according to an aspect of the present disclosure may be *Bacillus subtilis* MT2 strain (accession number: NITE BP-02767).

An anti-gram-negative bacterial agent according to an aspect of the present disclosure may include *Bacillus subtilis* MT2 strain (accession number: NITE BP-02767).

A beverage or food according to an aspect of the present disclosure may contain *Bacillus subtilis* MT2 strain (accession number: NITE BP-02767).

The present disclosure is also directed to a method for manufacturing an anti-gram-negative bacterial compound as described herein. The method may comprise culturing *Bacillus subtilis* and collecting a compound having the amino acid sequence represented by the chemical formula 1 produced by *Bacillus subtilis.*

The method for manufacturing anti-gram-negative bacterial compound according to an aspect of the present disclosure may comprise culturing *Bacillus subtilis* MT2 strain (accession number: NITE BP-02767) and collecting a compound having the amino acid sequence represented by the chemical formula 1 produced by *Bacillus subtilis* MT2 strain (accession number: NITE BP-02767).

The present disclosure is also directed to a method of using an anti-gram-negative bacterial compound as described herein to provide an anti-gram-negative bacterial agent.

The present disclosure is also directed to a method of using *Bacillus subtilis* as described herein to provide an anti-gram-negative bacterial agent.

The present disclosure is also directed to a method of using *Bacillus subtilis* MT2 strain (accession number: NITE BP-02767) to produce an anti-gram-negative bacterial agent as described herein.

The present disclosure is also directed to a method of treating enteritis. The method may comprise administering an anti-gram-negative bacterial compound having the amino acid sequence represented by the chemical formula 1 as described herein to a patient in need thereof. Additionally or alternatively, the method may comprise administering *Bacillus subtilis* capable of producing a compound having the amino acid sequence represented by the chemical formula 1 to a patient in need thereof. Additionally or alternatively, the method may comprise administering *Bacillus subtilis* MT2 strain (accession number: NITE BP-02767) to a patient in need thereof.

According to some aspects, the present disclosure provides an antimicrobial compound having a broad antimicrobial spectrum.

DETAILED DESCRIPTION

Figures 1A, 1B, 1C:
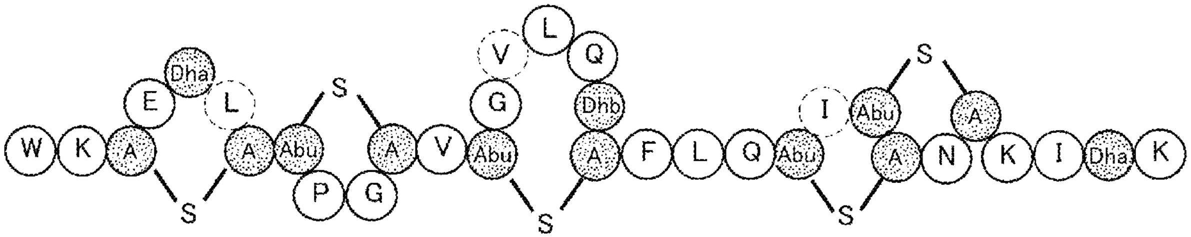
FIG. 1A shows a gene (SEQ ID NO: 1), which produces a bacteriocin as described herein.
FIG. 1B shows a prepeptide (SEQ ID NO: 3), of the bacteriocin of FIG. 1A.
FIG. 1C shows the active peptide of the bacteriocin of FIG. 1A.

Aspects of the present disclosure will be more specifically described below. However, it should be understood that while apparatuses and methods for realizing aspects of the present disclosure are described, the present disclosure is not necessarily limited to those apparatuses and methods alone.

An anti-gram-negative bacterial compound according to aspects of the present disclosure may have the amino acid sequence represented by chemical formula 1. The amino acid sequence represented by the chemical formula 1 is $C_{150}H_{231}N_{39}O_{38}S_5$. The anti-gram-negative bacterial compound according to aspect of the present disclosure may have an antimicrobial activity against gram-negative bacteria, fungi and gram-positive bacteria.

(1)

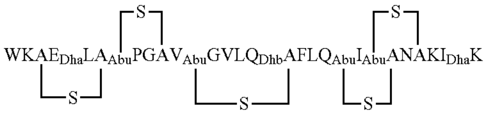

Non-limiting examples of gram-negative bacteria against which the anti-gram-negative bacterial compound according to the present disclosure has antimicrobial activity is a bacterium of the genus *Vibrio*. Examples of the bacterium of the genus *Vibrio* include, but are not limited to, *Vibrio parahaemolyticus, Vibrio cholerae*, Non-O1 *Vibrio cholerae, Vibrio mimicus, Vibrio fluvialis, Vibrio vulnificus, Vibrio alginolyticus, Vibrio parahaemolyticus* and *Vibrio furnissii.*

Non-limiting examples of fungus against which the anti-gram-negative bacterial compound according to the present disclosure has an antimicrobial activity is a fungus of the genus *Trichophyton*. Examples of the fungus of the genus *Trichophyton* include, but are not limited to, *Trichophyton rubrum, Trichophyton mentagrophytes, Trichophyton interdigitale, Trichophyton* spp. and *Trichophyton verrucosum.*

Non-limiting examples of the gram-positive bacteria against which the anti-gram-negative bacterial compound according to the present disclosure has an antimicrobial activity is a bacterium of the genus *Bacillus*. Examples of the bacterium include, but are not limited to, those of the genus *Bacillus* include *Bacillus subtilis, Bacillus cereus, Bacillus anthracis* and *Bacillus stearothermophilus. Bacillus subtilis* adversely affects soy sauce and miso production processes.

The anti-gram-negative bacterial compound according to the present disclosure may be produced, for example, by *Bacillus subtilis*. Although the anti-gram-negative bacterial compound according to the present disclosure may be derived from a gram-positive bacterium, *Bacillus subtilis*, the compound exerts the same level antimicrobial activity against not only gram-positive bacteria but also gram-negative bacteria and fungi. Accordingly, it is not necessary to use the anti-gram-negative bacterial compound as described herein in combination with a treatment for assisting antimicrobial activity against gram-negative bacteria.

One example treatment for assisting antimicrobial activity against gram-negative bacteria is the addition of a preservative such as a food preservative. Examples of preservatives include, but are not limited to, a chelating agent, a surfactant, an acid and a salt. Examples of chelating agents include ethylenediamine tetra acetate (EDTA). Examples of surfactantd include Tween 80. Examples of acids and salts include lactic acid, citric acid, pyrophosphoric acid, gluconic acid, acetic acid, nitrilotriacetic acid, hypochlorous acid, sorbic acid, benzoic acid and polyphosphoric acid, and salts thereof, and trisodium phosphate.

It is known that preservatives destabilize the adventitia of gram-negative bacteria, and as such, prior to the present invention, preservatives were thought to be necessary for sterilizing gram-negative bacteria with a bacteriocin derived from a gram-positive bacterium. In contrast, the anti-gram-negative bacterial compound according to the present disclosure can produce an effective antimicrobial action against gram-negative bacteria even if the compound is not used in combination with a preservative.

Another example of a treatment for assisting antimicrobial activity against gram-negative bacteria is the addition of a plant essential oil. Examples of the plant essential oils include oregano essential oil and thyme essential oil. Thymol and carvacrol contained in plant essential oil are considered to destabilize the adventitia of gram-negative bacteria. However, the anti-gram-negative bacterial compound according to the present disclosure can produce an effective antimicrobial action against gram-negative bacteria even if it is not used in combination with a plant essential oil.

Another example of treatment for assisting antimicrobial activity against gram-negative bacteria is high pressure treatment. High pressure treatment is treatment with the application of a pressure of, for example, 30 MPa or more. It is considered that application of high pressure destabilizes the adventitia of gram-negative bacteria. However, the anti-gram-negative bacterial compound according to the present disclosure can produce an effective antimicrobial activity against gram-negative bacteria even if high pressure treatment is not used in combination.

Other examples of treatment for assisting antimicrobial activity against gram-negative bacteria are high-temperature and low-temperature treatments. It is considered that high-temperature and low-temperature treatments destabilize the adventitia of gram-negative bacteria. Another example of treatment for assisting an antimicrobial activity against gram-negative bacteria is treatment with a pulse electric field. Treatment with a pulse electric field is considered to have the same level effect as high-temperature treatment because it raises the temperature of gram-negative bacteria. However, the anti-gram-negative bacterial compound according to the present disclosure can produce an effective antimicrobial action against gram-negative bacteria even if a high-temperature treatment, a low-temperature treatment, and/or pulse electric field treatment is not used in combination.

*Bacillus subtilis* capable of producing the anti-gram-negative bacterial compound according to the present disclosure has a bacteriocin-producing gene represented by, for example, the sequence shown in FIG. 1A and SEQ ID NO:1. In the sequence represented by SEQ ID NO: 1, the sequence from positions 1 to 72 encodes a leader peptide. The remaining gene sequence is represented by SEQ ID NO: 2. *Bacillus subtilis* capable of producing the anti-gram-negative bacterial compound according to the present disclosure may have a gene sequence represented by SEQ ID NO: 2.

The producer gene represented by the sequence shown in FIG. 1A and SEQ ID NO:1 is transcribed and translated to produce a prepeptide of a bacteriocin represented by the sequence shown in FIG. 1B and SEQ ID NO: 3. In the sequence represented by SEQ ID NO: 3, the sequence from positions 1 to 24 represents a leader peptide. The remaining amino acid sequence is represented by SEQ ID NO: 4.

When the leader peptide is cleaved off from the prepeptide of the bacteriocin represented by the sequence shown: in FIG. 1B and SEQ ID NO:3 by post-translational modification, an active peptide shown in FIG. 1C and having the sequence represented by the chemical formula 1 may be produced.

Serine at position 3 in the prepeptide represented by SEQ ID NO: 4 may be replaced by alanine in the active peptide. Serine at position 5 in the prepeptide represented by SEQ ID NO: 4 may be replaced by dehydroalanine in the active peptide. Cysteine at position 7 in the prepeptide represented by SEQ ID NO: 4 may be replaced by alanine in the active peptide. Threonine at position 8 in the prepeptide represented by SEQ ID NO: 4 may be replaced by aminobutyric acid in the active peptide.

Cysteine at position 11 in the prepeptide represented by SEQ ID NO: 4 may be replaced by alanine in the active peptide. Threonine at position 13 in the prepeptide represented by SEQ ID NO: 4 may be replaced by aminobutyric acid in the active peptide. Threonine at position 18 in the prepeptide represented by SEQ ID NO: 4 may be replaced by dehydrobutyrine in the active peptide. Cysteine at position 19 in the prepeptide represented by SEQ ID NO: 4 may be replaced by alanine in the active peptide.

Threonine at position 23 in the prepeptide represented by SEQ ID NO: 4 may be replaced by aminobutyric acid in the active peptide. Threonine at position 25 in the prepeptide represented by SEQ ID NO: 4 may be replaced by aminobutyric acid in the active peptide. Cysteine at position 26 in the prepeptide represented by SEQ ID NO: 4 may be replaced by alanine in the active peptide. Cysteine at position 28 in the prepeptide represented by SEQ ID NO: 4 may be replaced by alanine in the active peptide. Serine at position 31 in the prepeptide represented by SEQ ID NO: 4 may be replaced by dehydroalanine in the active peptide.

In the active peptide, alanine corresponding to serine at position-3 of the sequence of the prepeptide represented by SEQ ID NO: 4 may be bound to alanine corresponding to cysteine at position-7 of the sequence of the prepeptide represented by SEQ ID NO: 4, via a thioether bond, to produce lanthionine.

In the active peptide, aminobutyric acid corresponding to threonine at position 8 in the prepeptide represented by SEQ ID NO: 4 may be bound to alanine corresponding to cysteine at position 11 in the prepeptide represented by SEQ ID NO: 4 via a thioether bond to produce 3-methyllanthionine.

In the active peptide, aminobutyric acid corresponding to threonine at position 13 in the prepeptide represented by SEQ ID NO: 4 may be bound to alanine corresponding to cysteine at position 19 in the prepeptide represented by SEQ ID NO:4 via a thioether bond to produce 3-methyllanthionine.

In the active peptide, aminobutyric acid corresponding to threonine at t position 23 in the prepeptide represented by SEQ ID NO: 4 may be bound to alanine corresponding to cysteine at position 26 in the prepeptide represented by SEQ ID NO: 4 via a thioether bond to produce 3-methyllanthionine.

In the active peptide, aminobutyric acid corresponding to threonine at position 25 in the prepeptide represented by SEQ ID NO: 4 may be bound to alanine corresponding to cysteine at position 28 in the prepeptide represented by SEQ ID NO:4 via a thioether bond to produce 3-methyllanthionine.

*Bacillus subtilis* MT2 strain, which is one of *Bacillus subtilis* capable of producing the anti-gram-negative bacterial compound according to the present disclosure has been internationally deposited at the National Institute of Technology and Evaluation (Room 122, Kazusa-Kamatari 2-5-8, Kisarazu city, Chiba 292-0818, Japan) and accession number of NITE BP-02767 has been assigned. *Bacillus subtilis* MT2 strain was domestically deposited on Aug. 22, 2018 (domestic deposit date) at the National Institute of Technology and Evaluation (Japan) and transfer to international deposit was requested on Oct. 4, 2018 to the National Institute of Technology and Evaluation (Japan), based on the Budapest treaty. Access to deposited material will be available, during pendency of a patent application making reference to it, to anyone determined by the Director to be entitled to access under 37 CFR 1.14 and 35 U.S.C. 122. Subject to paragraph (b) of 37 CFR 1.808, all restrictions imposed by the depositor on the availability to the public of the deposited material will be irrevocably removed upon the granting of the patent. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit for the enforceable life of the patent, whichever period is longer.

The anti-gram-negative bacterial compound according to the present disclosure may be provided as a consumable product. For example, the anti-gram-negative bacterial compound may be contained in a medicament, a food, or a beverage.

The medicaments containing the anti-gram-negative bacterial compound according to the present disclosure may be used as disinfectants for gram-negative bacteria, gram-positive and bacteria fungi. The medicaments containing the anti-gram-negative bacterial compound according to the present disclosure may be used as therapeutic agents for pneumonia, food poisoning and enteritis. The medicaments containing the anti-gram-negative bacterial compound according to the present disclosure may be used as therapeutic agents for mycosis such as trichophytosis, candidiasis, cryptococcosis and aspergillosis.

Medicaments according to the present disclosure may contain an effective amount of the anti-gram-negative bacterial as described herein. The effective amount refers to the amount required for producing an antimicrobial action and may be appropriately determined depending on, e.g., the target microbe and symptom; and the age, body weight and gender of the patient.

As used herein, a "medicament" according to the present disclosure may comprise, for example, a pharmaceutically acceptable carrier such as tablets, capsules, liquids, creams, ointments, plaster, gels, waxes, and/or spray. The medicaments according to the present disclosure may be provided as, for example, disinfectants, oral medicines, external medicines such as liniments and/or eye drops. The medicaments according to the present disclosure may be applied to, for example, the internal organs such as intestine, and/or human skin including limbs, hair, oral cavity and eyeball. The disinfectant according to the present disclosure may be applied to, for example, foods, cooking utensils, walls and/or floors of a building (including but not limited to a hospital) and furniture (including but not limited to a desk).

The medicaments according to the present disclosure may contain ingredients of a medicament such as an oil, a fat, a wax, a hydrocarbon, a higher fatty acid, a higher alcohol, an ester, silicone, a moisturizer, a water-soluble polymer, a thickener, a coating agent, a sequestrant, a lower alcohol, a polyhydric alcohol, a sugar, an amino acid, an organic amine, a pH regulator, a skin nutritional supplement, a vitamin, a fragrance, a powder, a color material and/or water, depending on the purpose.

Additionally or alternatively, the anti-gram-negative bacterial compound according to the present disclosure may be provided as a food or beverage, that is, with a carrier selected from a beverage and/or a food. Additionally or alternatively, the anti-gram-negative bacterial compound according to the present disclosure may be provided with a carrier such as, e.g., toothpastes and/or oral cleansers.

*Bacillus subtilis* capable of producing the anti-gram-negative bacterial compound according to the present disclosure may be contained in medicaments, beverages and/or foods. *Bacillus subtilis* contained in, for example, medicaments, beverages and/or foods may produce the anti-gram-negative bacterial compound and exert an antimicrobial action against gram-negative bacteria, fungi and/or gram-positive bacteria. For example, the target diseases, dosage forms and dosages of medicaments containing *Bacillus subtilis* capable of producing the anti-gram-negative bacterial compound according to the present disclosure may be the same as those of the medicaments containing the anti-gram-negative bacterial compound according to the present disclosure.

*Bacillus subtilis* MT2 strain (accession number: NITE BP-02767) may be contained in medicaments, beverages and/or foods, as described herein. The target diseases, dosage forms and dosages of the medicaments containing *Bacillus subtilis* MT2 strain (accession number: NITE BP-02767) may be the same as those of the medicaments containing the anti-gram-negative bacterial compound according to the present disclosure.

The anti-gram-negative bacterial compound according to the present disclosure may be manufactured by culturing, for example, *Bacillus subtilis*, in a medium, and collecting a peptide having the amino acid sequence represented by the chemical formula 1 and produced by *Bacillus subtilis* in the medium. A method for collecting and purifying the peptide from the medium is not particularly limited. The anti-gram-negative bacterial compound according to the present disclosure may be chemically synthesized.

As described in the above, the anti-gram-negative bacterial compounds according to present disclosure may be used alone or in combination with one or more of the components as described herein and may produce the constitutions and functional effects shown in the following examples.

The anti-gram-negative bacterial compound according to the present disclosure may be an anti-gram-negative bacterial compound having the amino acid sequence represented by the chemical formula 1. The anti-gram-negative bacterial compound according to the present disclosure may have antimicrobial activities against gram-negative bacteria, gram-positive bacteria and/or fungi.

The anti-gram-negative bacterial compound according to the present disclosure may be produced by *Bacillus subtilis*. The anti-gram-negative bacterial compound according to the present disclosure may be produced by *Bacillus subtilis* MT2 strain (accession number: NITE BP-02767). Although the anti-gram-negative bacterial compound according to the present disclosure is derived from gram-positive bacteria, *Bacillus subtilis*, the compound has an antimicrobial activity against gram-negative bacteria.

The gram-negative bacteria against which the anti-gram-negative bacterial compound according to the present disclosure produces an antimicrobial activity may be a bacterium of the genus *Vibrio*. The bacterium of the genus *Vibrio* may be *Vibrio parahaemolyticus*.

The fungus against which the anti-gram-negative bacterial compound according to the present disclosure produces an antimicrobial activity may be a fungus of the genus *Trichophyton*. The fungus of the genus *Trichophyton* may be *Trichophyton rubrum, Trichophyton mentagrophytes* or *Trichophyton interdigitale*.

The anti-gram-negative bacterial compound according to the present disclosure may optionally be d used without a treatment for assisting antimicrobial activity against gram-negative bacteria as described herein. For example, the treatment for assisting antimicrobial activity against gram-negative bacteria may be the addition of a preservative. The preservative may be a chelating agent. Even if the anti-gram-negative bacterial compound according to the present disclosure is not used in combination with a treatment for assisting antimicrobial activity against gram-negative bacteria, the compound may exert the same level of antimicrobial activity against gram-positive bacteria and gram-negative bacteria.

An anti-gram-negative bacterial agent according to an present disclosure may contain an anti-gram-negative bacterial compound as described herein. Beverages or foods according to the present disclosure may contain an anti-gram-negative bacterial compound as described herein.

*Bacillus subtilis* according to the present disclosure may be that capable of producing a compound having the amino acid sequence represented by the chemical formula 1.

The anti-gram-negative bacterial agent according to the present disclosure may contain *Bacillus subtilis* capable of producing the compound having the amino acid sequence represented by the chemical formula 1. Beverages or foods according to the present disclosure may contain *Bacillus subtilis* capable of producing the compound having the amino acid sequence represented by the chemical formula 1.

*Bacillus subtilis* according to the present disclosure may be *Bacillus subtilis* MT2 strain (accession number: NITE BP-02767).

The anti-gram-negative bacterial agent according to the present disclosure may contain *Bacillus subtilis* MT2 strain (accession number: NITE BP-02767) as described herein. The beverages or foods according to the present disclosure may contain *Bacillus subtilis* MT2 strain (accession number: NITE BP-02767) as described herein.

The method for manufacturing the anti-gram-negative bacterial compound as described herein may include culturing *Bacillus subtilis* and collecting a compound having the amino acid sequence represented by the chemical formula 1 and produced by *Bacillus subtilis.*

The method for producing the anti-gram-negative bacterial compound as described herein may include culturing *Bacillus subtilis* MT2 strain (accession number: NITE BP-02767) and collecting a compound having the amino acid sequence represented by the chemical formula 1 and produced by *Bacillus subtilis* MT2 strain (accession number: NITE BP-02767).

The present disclosure is also directed to the use of a bacteriocin of the anti-gram-negative bacterium as described herein in manufacturing an anti-gram-negative bacterial agent.

The present disclosure is also directed to the use of *Bacillus subtilis* capable of producing the compound having the amino acid sequence represented by the chemical formula 1 in manufacturing an anti-gram-negative bacterial agent.

The present disclosure is also directed to the use of *Bacillus subtilis* MT2 strain (accession number: NITE BP-02767) in manufacturing an anti-gram-negative bacterial agent as described herein.

A method for treating enteritis according to the present disclosure may include administering the anti-gram-negative bacterial compound as described herein to a patient in need thereof. A method for treating enteritis according to the present disclosure may include administering *Bacillus subtilis* capable of producing the compound having the amino acid sequence represented by the chemical formula 1 to a patient in need thereof. A method for treating enteritis according to the present disclosure may include administering *Bacillus subtilis* MT2 strain (accession number: NITE BP-02767) to a patient in need thereof. According to some aspects, the enteritis may be food poisoning.

The above disclosure is provided in order to facilitate understanding thereof and should not be construed as necessarily limiting the present invention. For example, the present disclosure may be modified or improved without deviating from the scope of the invention and may include equivalents of the invention. More specifically, embodiments appropriately modified in design by those skilled in the art are contained in the scope of the present disclosure as long as they have the features of the present disclosure. For example, elements, materials, conditions and dosage forms of the present disclosure are not necessarily limited to those mentioned herein and can be appropriately changed. In some instances, aspects of the present disclosure may be partially replaced with each other or used in combination as long as they have one or more features described herein.

EXAMPLES

Examples of the present disclosure will be described below. However, the present disclosure is not necessarily limited by the following Examples.

Example 1: Preparation of *Artemisia indica* var. *maximowiczii* fermentation liquid It is reported that the number of lactic acid bacteria in *Artemisia indica* var. *maximowiczii* leaves reaches a maximum during the time zone from one hour before to one hour after sunrise (2 hours in total) in a day; and that, in the other time zones, the number of lactic acid bacteria is low and the number of photosynthetic bacteria is high. Accordingly, portions about 20 cm from the tip of the *Artemisia indica* var. *maximowiczii* leaves were collected during the time zone of this 2 hours. Immediately upon collection, the *Artemisia indica* var. *maximowiczii* leaves (6.3 kg) were put in a first pickle barrel with a vinyl bag placed inside, and 3.2 kg of syrup and 0.6 kg of crude salt were sprinkled. Then, the vinyl bag was closed and sealed. Weight stone was placed on the vinyl bag to pickle *Artemisia indica* var. *maximowiczii* leaves.

Several days later, when *Artemisia indica* var. *maximowiczii* leaves were covered with juice derived from the leaves, the weight stone was removed. Subsequently, 10 L of chlorine-free rinse water was poured in a second pickle barrel, and *Artemisia indica* var. *maximowiczii* leaves (pickles) and 10 kg of the juice were put in the rinse water. Separately, a third pickle barrel was set up by placing a wire-mesh filter so as to cover the opening thereof. *Artemisia indica* var. *maximowiczii* leaves were taken out little by little from the second pickle barrel while washing and rubbing them by hand and put on the wire-mesh filter over the opening of the third pickle barrel and lightly pushed by hand to squeeze out the juice.

All leaves of *Artemisia indica* var. *maximowiczii* were squeezed and the juice remaining in the second pickle barrel was filtered by the wire-mesh filter. Subsequently, syrup (Hateruma brown sugar) was added to the juice in the third pickle barrel so as to obtain a final concentration of 10 wt % and crude salt was dissolved so as to obtain a final concentration of 3 wt %. Thereafter, the ambient temperature of the third pickle barrel was controlled to be about 30° C. to initiate fermentation. At first, large bubbles were released and then smaller-size bubbles gradually released. The bubbling was finally stopped. The pH of the juice when bubbling stopped (about one week later), was about 3.8. The juice obtained at this time was defined as *Artemisia indica* var. *maximowiczii* fermentation liquid.

Example 2: Preparation of *Bacillus subtilis*

To Lactobacilli MRS medium (1% of proteose peptone, 1% of beef extract, 0.5% of yeast extract, 2% of glucose, 0.1% of Tween 80, 0.5% of ammonium citrate, 0.01% of magnesium sulfate, 0.005% of manganese sulfate and 0.2% of dipotassium phosphate, manufactured by Difco), the *Artemisia indica* var. *maximowiczii* fermentation liquid was added dropwise and bacteria contained in the *Artemisia indica* var. *maximowiczii* fermentation liquid were cultured in the medium. Subculture was carried out several times as needed. Thereafter, the bacteria cultured were smeared onto Lactobacilli MR agar medium (medium prepared by adding 3% of agar to the aforementioned MRS medium) and cultured. From the generated colonies, bacteria were collected.

Subsequently, from the bacteria collected, a strain having an antimicrobial substance productivity was selected as *Bacillus subtilis* MT2 strain based on the antimicrobial activity against spore-forming lactic acid bacteria, i.e., *Bacillus coagulans*, as an index with Spot-on-lawn method. The mycological properties of the selected *Bacillus subtilis* MT2 strain was analyzed. The strain was identified as *Bacillus subtilis* based on homology analysis of a nucleotide sequence of 16 ribosome DNA (rDNA).

Figure 2:
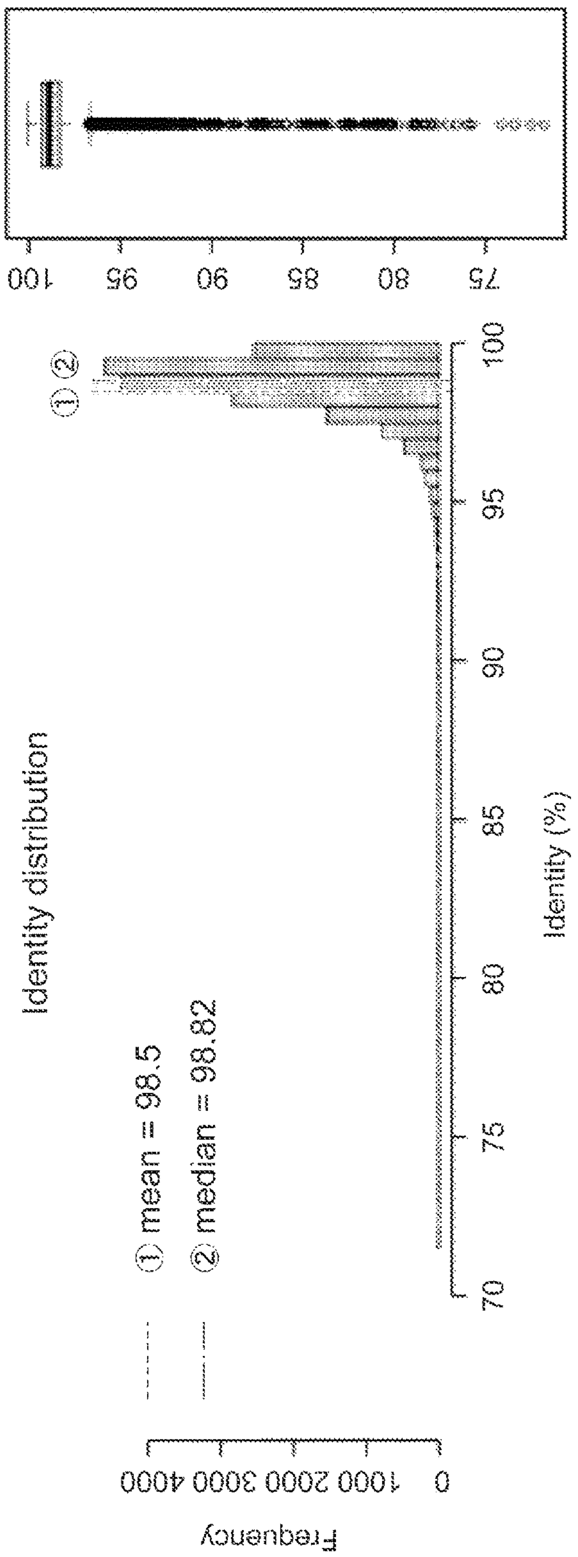
FIG. 2 is a graph showing the homology analysis results of whole genomic sequences of *Bacillus subtilis* MT2 strain and *Bacillus subtilis* subsp. *subtilis* 168 by the ANI method.

The mean "percent homology" of the whole genomic sequence of *Bacillus subtilis* MT2 strain with the whole genomic sequence of an existing *Bacillus subtilis* strain, i.e., *Bacillus subtilis* subsp. *subtilis* 168, was obtained in accordance with the ANI (average nucleotide identity) method. As a result, the mean "percent homology" was 98.5% as shown in FIG. 2. These sequences differed by 1.5%.

Figure 3:
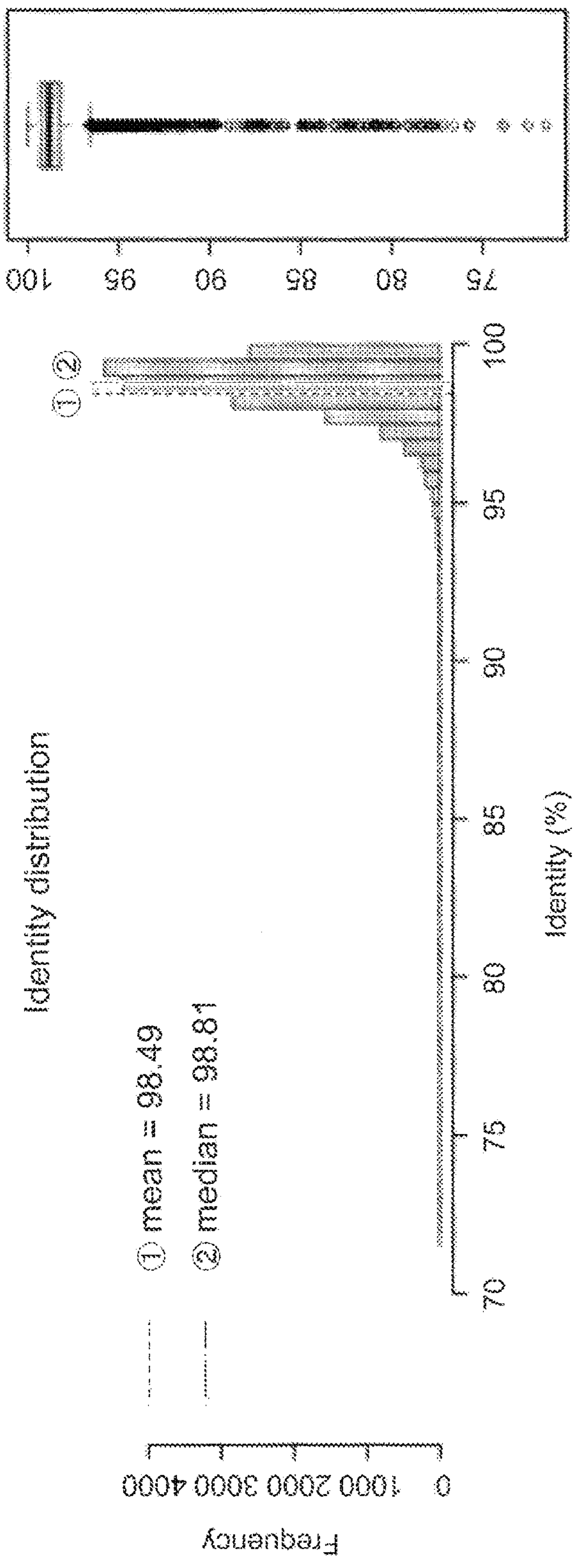
FIG. 3 is a graph showing the homology analysis results of whole genomic sequences of *Bacillus subtilis* MT2 strain and *Bacillus subtilis* subsp. *subtilis* 6051-HGW by the ANI method.

The mean "percent homology" of the whole genomic sequence of *Bacillus subtilis* MT2 strain with the whole genomic sequence of an existing *Bacillus subtilis* strain, i.e., *Bacillus subtilis* subsp. *subtilis* 6051-HGW, was obtained in accordance with the ANI method. As a result, the mean "percent homology" was 98.49% as shown in FIG. 3. These sequences differed by 1.51%.

Figure 4:
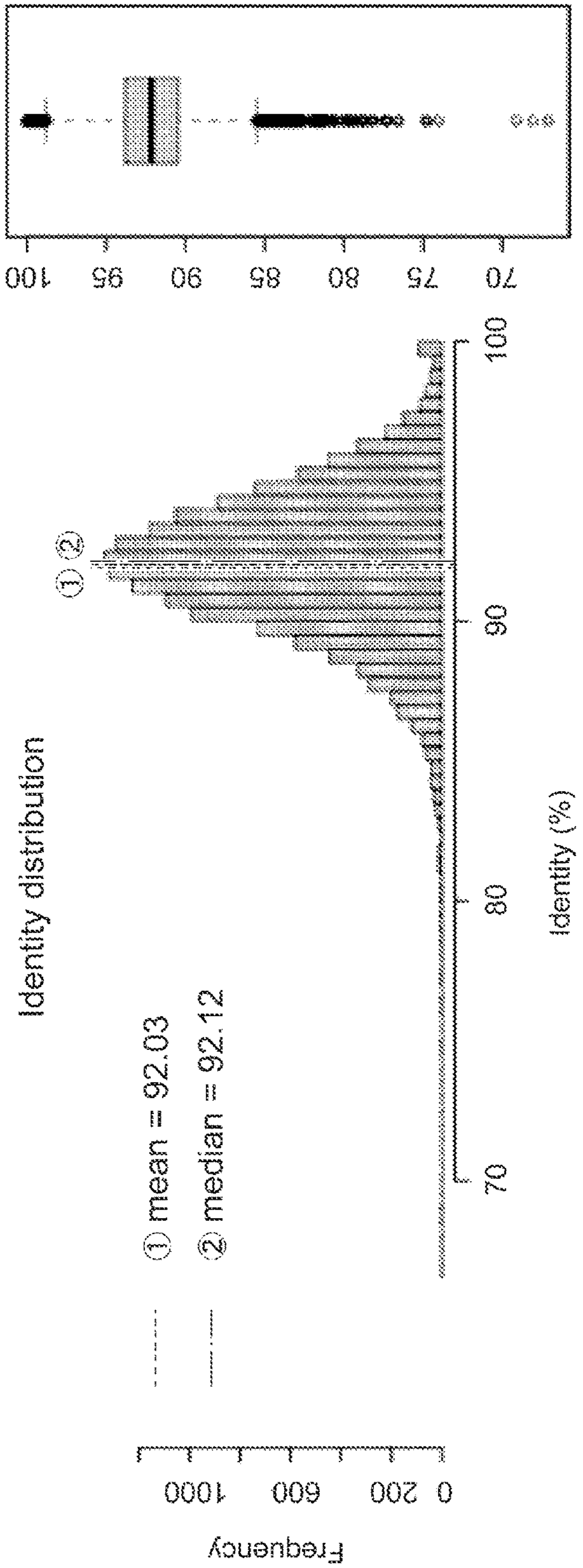
FIG. 4 is a graph showing the homology analysis results of whole genomic sequences of *Bacillus subtilis* MT2 strain and *Bacillus subtilis* subsp. *spizizenii* W23 by the ANI method.

The mean "percent homology" of the whole genomic sequence of *Bacillus subtilis* MT2 strain with the whole genomic sequence of an existing *Bacillus subtilis* strain, i.e., *Bacillus subtilis* subsp. *spizizenii* W23, was obtained in accordance with the ANI method. As a result, the mean "percent homology" was 92.03%, as shown in FIG. 4. These sequences differed by 7.97%.

Figure 5:
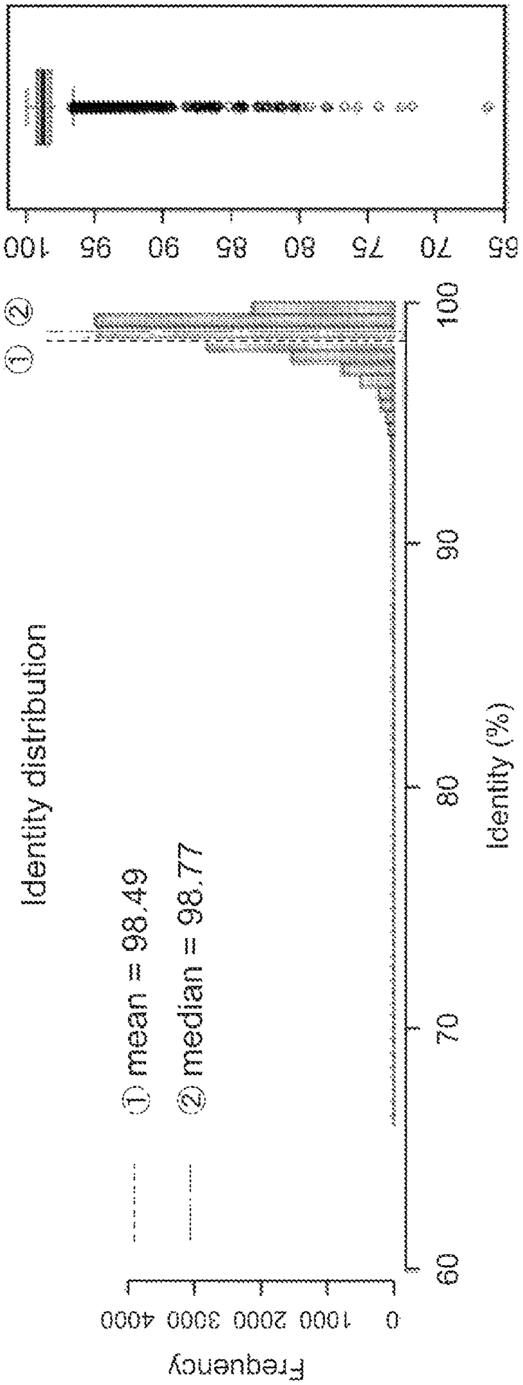
FIG. 5 is a graph showing the homology analysis results of whole genomic sequences of *Bacillus subtilis* MT2 strain and *Bacillus* tequilensis FJAT-14262a by the ANI method.

The mean "percent homology" of the whole genomic sequence of *Bacillus subtilis* MT2 strain with the whole genomic sequence of an existing *Bacillus subtilis* strain, i.e., *Bacillus* tequilensis FJAT-14262a, was obtained in accordance with the ANI method, the mean "percent homology" was 98.49%, as shown in FIG. 5. These sequences differ by 1.51%.

From comparison with the existing *Bacillus subtilis* strains, *Bacillus subtilis* MT2 strain was considered to be a novel strain of *Bacillus subtilis. Bacillus subtilis* MT2 strain was internationally deposited at the National Institute of Technology and Evaluation (Japan) and accession number: NITE BP-02767 was assigned. *Bacillus subtilis* MT2 strain has the gene sequence shown in SEQ ID NO:1 or 2.

Example 3: Preparation of bacteriocin

*Bacillus subtilis* MT2 strain was subjected to shaking culture carried out in Lactobacilli MRS medium at a temperature of 35° C. or more to 37° C. or less in an aerobic condition for 3 days. Thereafter, the medium containing the bacterial cells was centrifuged at 10,000 rpm and 25° C. for 20 minutes. The resultant (centrifuged) medium was filtered by a sterile filter having an opening of 0.45 μm to remove the bacterial cells. In this manner, culture supernatant was obtained.

Using a reversed-phase silica gel cartridge (Sep-Pac C18, manufactured by Millipore), a bacteriocin contained in the culture supernatant was concentrated. Further, an active bacteriocin fraction was separated by reversed-phase column chromatography using Sephasil Peptide C185μST (manufactured by Pharmacia).

Figure 6:
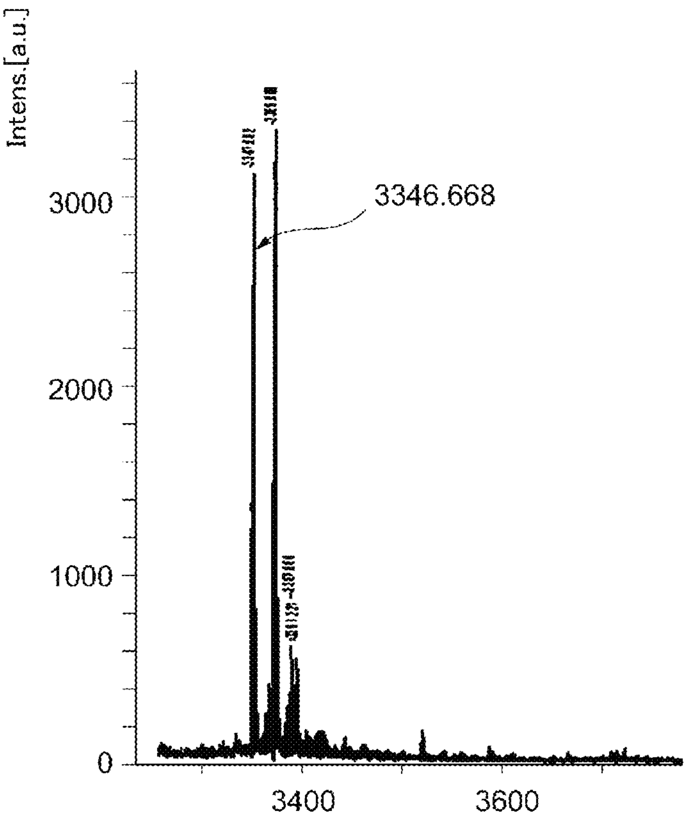
FIG. 6 is a graph showing the mass spectrometry results of a bacteriocin as described herein.

The active bacteriocin fraction separated was subjected to mass spectrometry using by a matrix-assisted laser desorption/ionization time-of-flight mass spectrometer (MALDI-TOFMS ultraflex III, manufactured by Bruker). As a result, the accurate molecular weight was about 3346, as shown in FIG. 6. Note that, as a target plate, MTP384 ground steel (Bruker daltonics) was used. As a matrix, α-cyan-4-hydroxycinnamic acid (HCCA) was used, after studies were repeatedly made. When the amino acid sequence of active bacteriocin fractioned was analyzed, the amino acid sequence represented by the chemical formula 1 was obtained.

Example 4: Antimicrobial activity of bacteriocin

Figure 7:
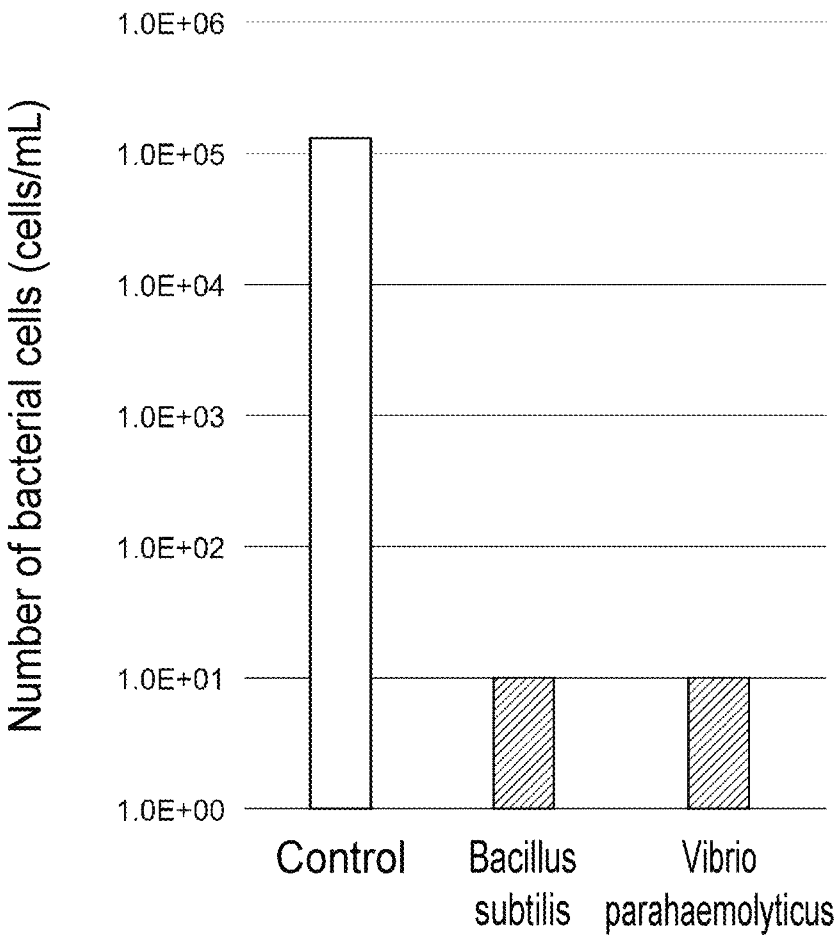
FIG. 7 is a graph showing the antimicrobial activity of a bacteriocin as described herein.

As a gram-positive bacterium, *Bacillus subtilis* (*Bacillus subtilis*, NBRC 3134) was used; and as a gram-negative bacterium, *Vibrio parahaemolyticus* (12711T) was used. To a 10 mL solution (pH7.8) containing the active bacteriocin prepared in Example 3, a bacterial emulsion (0.1 mL) containing either one of the aforementioned bacteria in a concentration of $10^7$ cells/mL was inoculated and allowed to stand still at 25° C. for 24 hours. After that, viable cell count was determined. As a control, to phosphate buffer (10 mL) having a concentration of 0.067 mol/L (pH7.2), 0.1 mL of a bacterial emulsion of *Vibrio parahaemolyticus,* 12711T, was inoculated and allowed to stand still at 25° C. for 24 hours. After that, viable cell count was determined. As a result, as shown in FIG. 7, the numbers of survival cells of *Bacillus subtilis* and *Vibrio parahaemolyticus* were both decreased the same level by the active bacteriocin.

Figure 8:
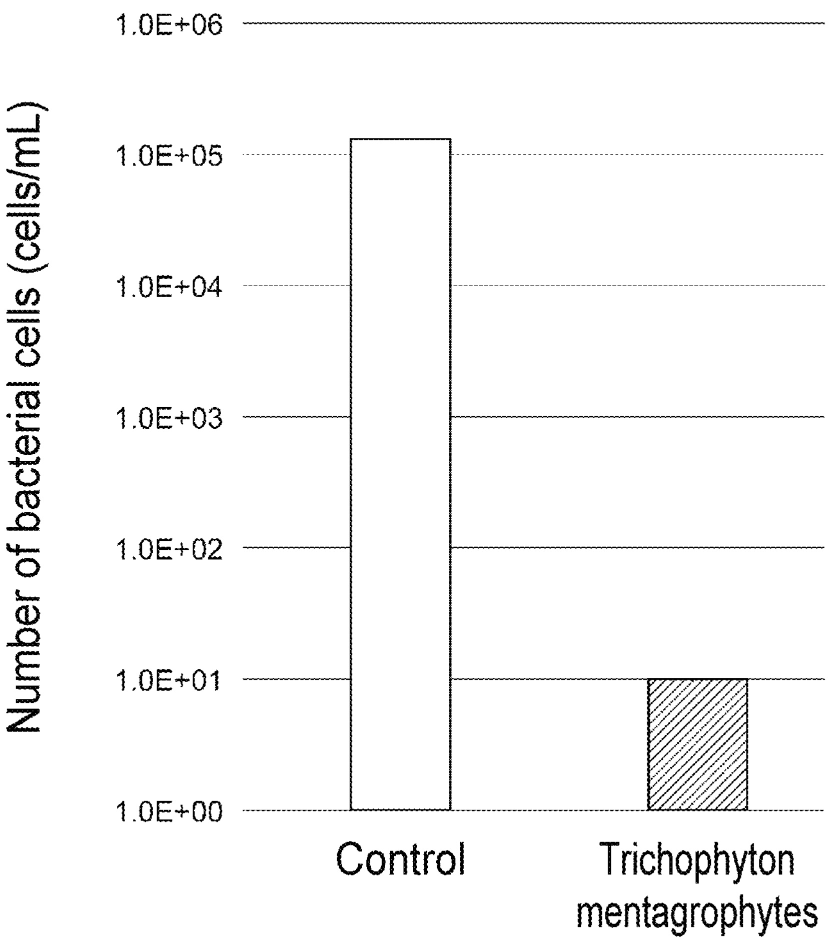
FIG. 8 is a graph showing the antimicrobial activity of bacteriocin as described herein.

Further, *Trichophyton mentagrophytes* (NBRC 6124) was used as a fungus. To a 10 mL solution (pH7.8) containing the active bacteriocin prepared in Example 3, a bacterial emulsion (0.1 mL) containing *Trichophyton mentagrophytes* in a concentration of $10^7$ cells/mL was inoculated and allowed to stand still at 25° C. for 24 hours. After that, viable cell count was determined. As a control, to phosphate buffer (10 mL) having a concentration of 0.067 mol/L (pH7.2), 0.1 mL of a bacterial emulsion of *Trichophyton mentagrophytes* (NBRC 6124) was inoculated and allowed to stand still at 25° C. for 24 hours. After that, viable cell count was determined. As a result, as shown in FIG. 8, the number of survival cells of *Trichophyton mentagrophytes* was decreased by the active bacteriocin.

The invention claimed is:

1. A composition comprising:

an anti-gram-negative bacterial compound having an amino acid sequence represented by chemical formula 1:

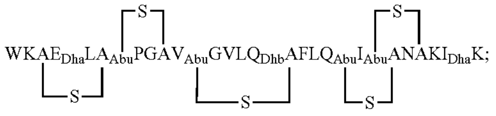

and a carrier comprising one or more of silicone, a moisturizer, a thickener, a coating agent, a sequestrant, a pH regulator, a skin nutritional supplement, a fragrance, a powder, and a color material;

wherein the composition is formulated as a cream, ointment, wax, or a combination thereof.

2. The composition according to claim 1, wherein the anti-gram-negative bacterial compound is produced by *Bacillus subtilis.*

3. The composition according to claim 1, wherein the anti-gram-negative bacterial compound is produced by *Bacillus subtilis* MT2 strain (accession number: NITE BP-02767).

4. The composition according to claim 1, wherein the anti-gram-negative bacterial compound has antimicrobial activity against a gram-negative bacterium of the genus *Vibrio.*

5. The composition according to claim 4, wherein the gram-negative bacterium is *Vibrio parahaemolyticus.*

6. The composition according to claim 1, wherein the anti-gram-negative bacterial compound has antimicrobial activity against a fungus.

7. The composition according to claim 6, wherein the fungus is of the genus *Trichophyton.*

8. The composition according to claim 7, wherein the fungus is *Trichophyton rubrum.*

9. The composition according to claim 7, wherein the fungus is *Trichophyton mentagrophytes* or *Trichophyton interdigitale*.

10. The composition according to claim 1, wherein the anti-gram-negative bacterial compound has antimicrobial activity against a gram-positive bacterium.

11. The composition to claim 1, wherein the composition is free of an additional treatment for assisting the anti-gram-negative bacterial compound against gram-negative bacteria.

12. The composition according to claim 11, wherein the treatment is a preservative comprising a chelating agent.

13. The composition according to claim 1, wherein the composition is formulated as a cream or an ointment, or a gel.

14. The composition according to claim 1, wherein the composition is formulated as a wax.

15. The composition according to claim 1, wherein the carrier comprises silicone.

16. The composition according to claim 1, wherein the carrier comprises a moisturizer.

17. The composition according to claim 1, wherein the carrier comprises a powder.

* * * * *